United States Patent [19]
Hsieh

[11] Patent Number: 5,533,081
[45] Date of Patent: Jul. 2, 1996

[54] GUIDED RINGFIX ALGORITHM FOR IMAGE RECONSTRUCTION

[75] Inventor: Jiang Hsieh, Waukesha, Wis.

[73] Assignee: General Electric Company, Milwaukee, Wis.

[21] Appl. No.: 373,410

[22] Filed: Jan. 17, 1995

[51] Int. Cl.$^6$ ............................................ A61B 6/03
[52] U.S. Cl. .................. 378/15; 378/901; 364/413.16; 364/413.17
[58] Field of Search ................... 378/4, 15, 901; 364/413.14, 413.15, 413.16, 413.17

[56] References Cited

U.S. PATENT DOCUMENTS

| | | | |
|---|---|---|---|
| 4,071,760 | 1/1978 | LeMay | 378/4 |
| 4,670,840 | 6/1987 | Freundlich | 364/413.19 |
| 5,301,108 | 4/1994 | Hsieh | 364/413.19 |
| 5,473,656 | 12/1995 | Hsieh et al. | 378/4 |

*Primary Examiner*—David P. Porta
*Assistant Examiner*—David Vernon Bruce
*Attorney, Agent, or Firm*—John S. Beulick; John H. Pilarski

[57] ABSTRACT

A present invention, in one form, is a method for removing artifacts from image data due to detector degradation. Particularly, data is obtained from a CT system including a detector and an x-ray source. The detector is formed from a plurality of detector cells. In accordance with one form of the invention, a detector degradation signature ($S(i)$) vector is generated prior to scanning a patient. Subsequent to scanning the patient, if the image data contains a ring error, a detector cell contributing to the error is identified using the detector degradation signature vector. The system then determines if the cell a degraded cell. If such cell is a degraded cell, ring error correction processing is then performed on the image data.

13 Claims, 5 Drawing Sheets

GUIDED RINGFIX ALGORITHM FOR IMAGE RECONSTRUCTION

FIELD OF THE INVENTION

This invention relates generally to computed tomography (CT) imaging and more particularly, to the reconstruction of images from projection data in a manner that corrects the data due to errors resulting from degraded detectors.

BACKGROUND OF THE INVENTION

In CT systems, an x-ray source projects a fan-shaped beam which is collimated to lie within an X-Y plane of a Cartesian coordinate system, termed the "imaging plane". The x-ray beam passes through the object being imaged, such as a patient, and impinges upon a linear array of radiation detectors. The intensity of the transmitted radiation is dependent upon the attenuation of the x-ray beam by the object. Each detector of the linear array produces a separate electrical signal that is a measurement of the beam attenuation. The attenuation measurements from all the detectors are acquired separately to produce a transmission profile.

The x-ray source and the linear detector array in a CT system are rotated with a gantry within the imaging plane and around the object so that the angle at which the x-ray beam intersects the object constantly changes. A group of x-ray attenuation measurements from the detector array at one gantry angle is referred to as a "view". A "scan" of the object comprises a set of views made at different gantry angles during one revolution of the x-ray source and detector. In an axial scan, data is processed to construct an image that corresponds to a two dimensional slice taken through the object. One method for reconstructing an image from a set of data is referred to in the art as the filtered back projection technique. This process converts the attenuation measurements from a scan into integers called "CT numbers" or "Hounsfield units", which are used to control the brightness of a corresponding pixel on a cathode ray tube display.

Detector arrays are constructed from a plurality of detectors cells. The cells may deteriorate to the extent that artifacts are introduced to the images. Visually, these artifacts may appear as rings or bands in an image. Particularly, the lack of uniformity across the detector array and the lack of similarity among the degraded cells causes artifacts in the shape of rings or bands when a sloped object is scanned. It is desirable, of course, to minimize artifacts in an image.

Known algorithms exist for removing the rings from an image. Particularly, the rings may be detected and corrected in the projection space or in the image space. For example, in a known projection space correction algorithm, an "error candidate vector" is generated based on the filtration of pre-processed projections. The vector is then compared to the vectors generated from previous views to determine the amount of the correction required. Such an algorithm is described in U.S. Pat. No. 5,301,108, which is assigned to the present assignee.

With another known ringfix algorithm, a ring is identified by performing a high pass radial filtering. In the actual implementation, the radial filter is approximated by the weighted sum of horizontal and vertical one dimensional filters. Based on the filtering result and predefined criteria, errors in each previously defined segment in the image is azimuthally combined to determine the ring error for the entire segment. Ring artifacts are removed by subtracting the error from the original image on a segment by segment basis.

With known algorithms, the filter length cannot be adapted as a function of pixel size. Particularly, the kernel size and shape of the high pass filter is kept constant. This is non-optimal since the frequency response of the high pass filter depends strongly on the image pixel size. To maintain a relatively constant frequency response of the filter over the entire display field of view (DFOV), the kernel size of the boxcar filter needs to vary as a function of the DFOV.

Another shortcoming of known algorithms is that such algorithms cannot be adapted to the error patterns. The width of a ring generated by an isolated channel will be roughly half as wide as the one generated by two adjacent channels. Therefore, in order to ensure that the filter can detect and correct double cell rings as effectively as the single cell rings, the filter length has to be adjusted accordingly. Naturally, this requires a-priori knowledge of the detector characteristics.

Yet another shortcoming of known algorithms is their inability to deal with rings of high magnitude. Whenever a deep ring is present in the image, the known ringfix algorithms will correct it only to the extent of reducing its magnitude. After the ringfix correction, the residual ring is still quite visible. For many rings associated with degraded detectors, the magnitude of the rings are fairly deep and therefore cannot be corrected by the existing ringfix algorithms.

SUMMARY OF THE INVENTION

The present algorithm, in one form, includes generating a detector degradation signature (S(i)) vector. Such vector is identified prior to scanning a patient. In reconstructing an image from data obtained during a scan, and if a detector cell or channel i under examination is a degraded channel based on the vector S(i). the magnitude of the ring error for channel i associated with each ring segment is examined. If the magnitude of such error for a channel i is larger than a predefined threshold, the error data for the neighboring rings in the segment (including the ring associated with channel i) are modified. The ring error is then eliminated by subtracting the error data, as modified, from the image data. The true image is then reconstructed from the corrected image data.

The present ring correction algorithm is not only effective in removing ring artifacts related to the degraded detectors, but also has a minimal impact on the processing requirements of reconstructing an image. Further, the vector S(i) may be used to adapt the filter kernel used to detect rings in an image. The filter kernel may also be modified based on the reconstruction DFOV and the reconstruction kernel type as explained hereinafter in more detail.

DETAILED DESCRIPTION OF THE DRAWING

Figure 1:
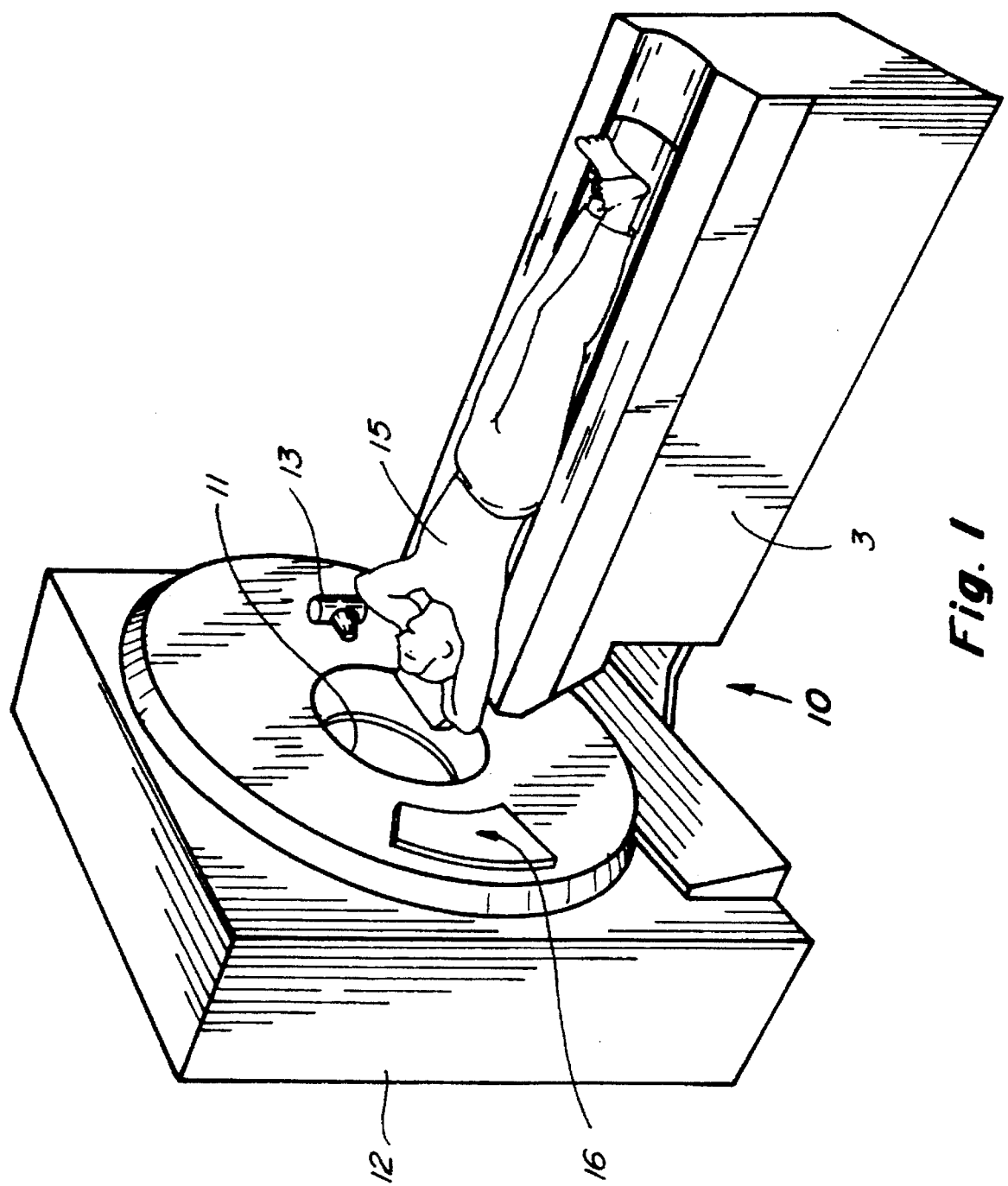
FIG. 1 is a pictorial view of a CT imaging system in which the present invention may be employed.
Figure 2:
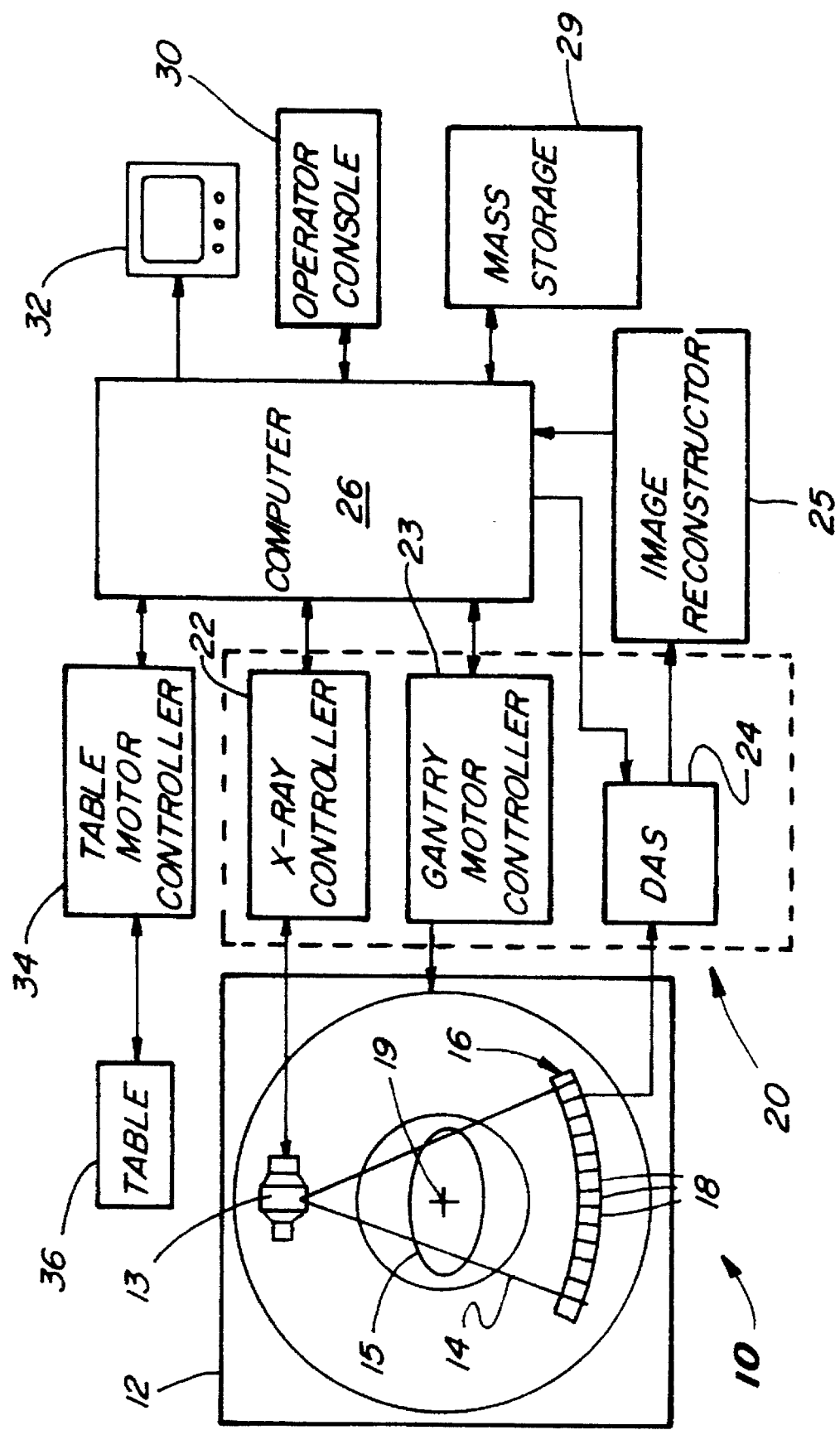
FIG. 2 is a block schematic diagram of the CT imaging system illustrated in FIG. 1.

With reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of gantry 12. Detector array 16 is formed by two rows of detector elements 18 which together sense the projected x-rays that pass through a medical patient 15. Each detector element 18 produces an electrical signal that represents the intensity of an impinging x-ray beam and hence the attenuation of the beam as it passes through patient 15. During a scan to acquire x-ray projection data, gantry 12 and the components mounted thereon rotate about a center of rotation 19.

Rotation of gantry 12 and the operation of x-ray source 13 are governed by a control mechanism 20 of CT system 10. Control mechanism 20 includes an x-ray controller 22 that provides power and timing signals to x-ray source 13 and a gantry motor controller 23 that controls the rotational speed and position of gantry 12. A data acquisition system (DAS) 24 in control mechanism 20 samples analog data from detector elements 18 and converts the data to digital signals for subsequent processing. An image reconstructor 25 receives sampled and digitized x-ray data from DAS 24 and performs high speed image reconstruction. The reconstructed image is applied as an input to a computer 26 which stores the image in a mass storage device 29.

Computer 26 also receives commands and scanning parameters from an operator via console 30 that has a keyboard. An associated cathode ray tube display 32 allows the operator to observe the reconstructed image and other data from computer 26. The operator supplied commands and parameters are used by computer 26 to provide control signals and information to DAS 24, x-ray controller 22 and gantry motor controller 23. In addition, computer 26 operates a table motor controller 34 which controls a motorized table 36 to position patient 15 in gantry 12.

Figure 3:
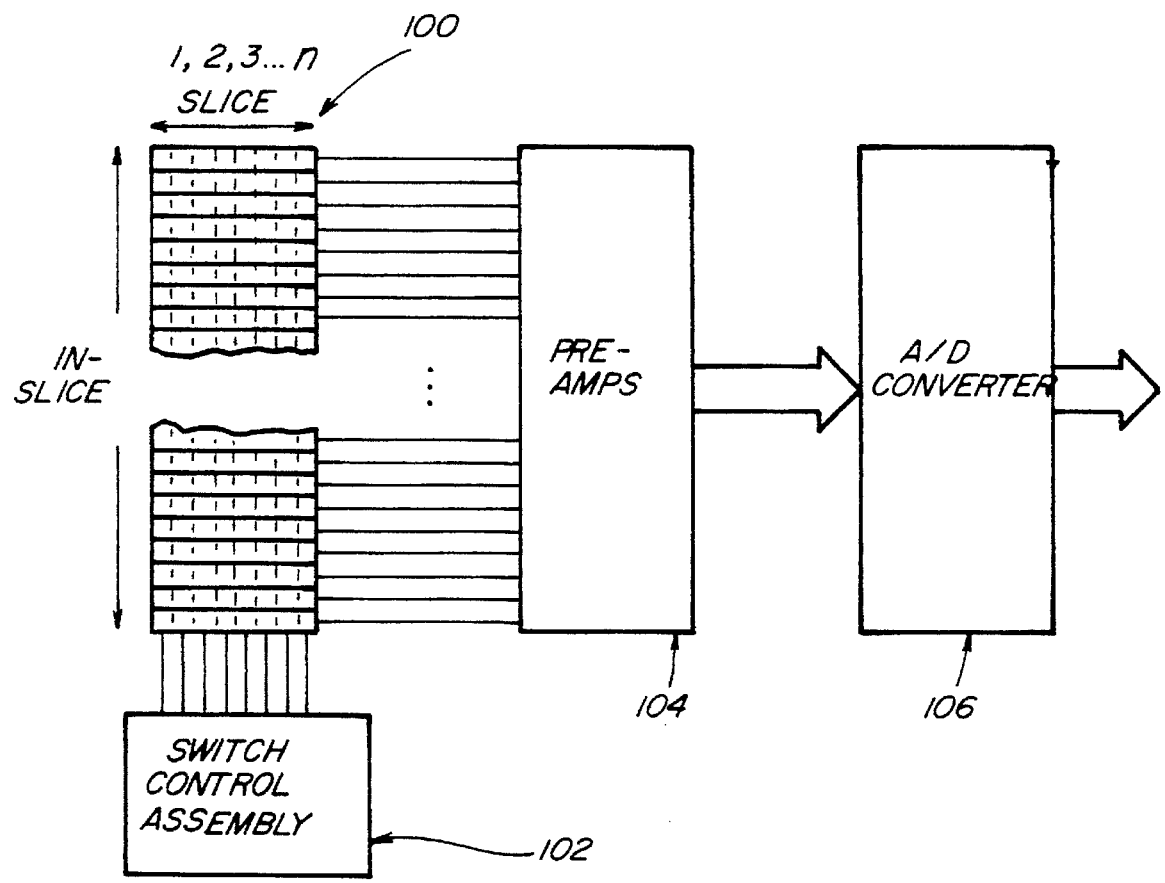
FIG. 3 is a block diagram depiction of detector cells of a detector and related controls.

FIG. 3 illustrates a detector 100 coupled to a switch control assembly 102. Detector 100 is composed of a plurality of detector cells arranged in rows. As explained above, each detector cell produces an electrical signal that represents the intensity of an impinging x-ray beam and hence the attenuation of the beam as it passes through a patient. The output of each cell is supplied to a preamplifier 104 which supplies an amplified signal to an analog-to-digital converter 106. The digitized signal is then supplied to other components (not shown) for further processing and image reconstruction.

Detector 100 is illustrated for explanation purposes only. The present algorithm can be used in connection with many other detector configurations. For example, it is contemplated that rather than a detector with a plurality of cells in the slice (horizontal) dimension, i.e., a two-dimensional detector, a detector with only one cell in such dimension, i.e., a one-dimensional, detector may be used.

The detector cells may deteriorate to the extent that artifacts are introduced to the images. As explained above, these artifacts may appear as rings or bands in an image. The lack of uniformity across the detector array and the lack of similarity among the degraded cells, for example, cause artifacts in the shape of rings or bands when a sloped object is scanned.

The present algorithm is directed to removing such artifacts from the image data. Unlike known ringfix algorithms based on the assumption that each detector cell or channel has an equal probability of producing the error, the present algorithm uses a-priori knowledge to determine whether a detector cell is, in fact, degraded. Rather than estimating ring error regardless of which detector channel produces the error, the present algorithm performs a separate ringfix correction only for data associated with a degraded cell. By knowing ahead of time that certain detector channels are degraded, the error detection and correction process can be optimized to tailor to the degraded channels. In other words the information related to the detector health is utilized to "guide" the ringfix process.

Figure 4:
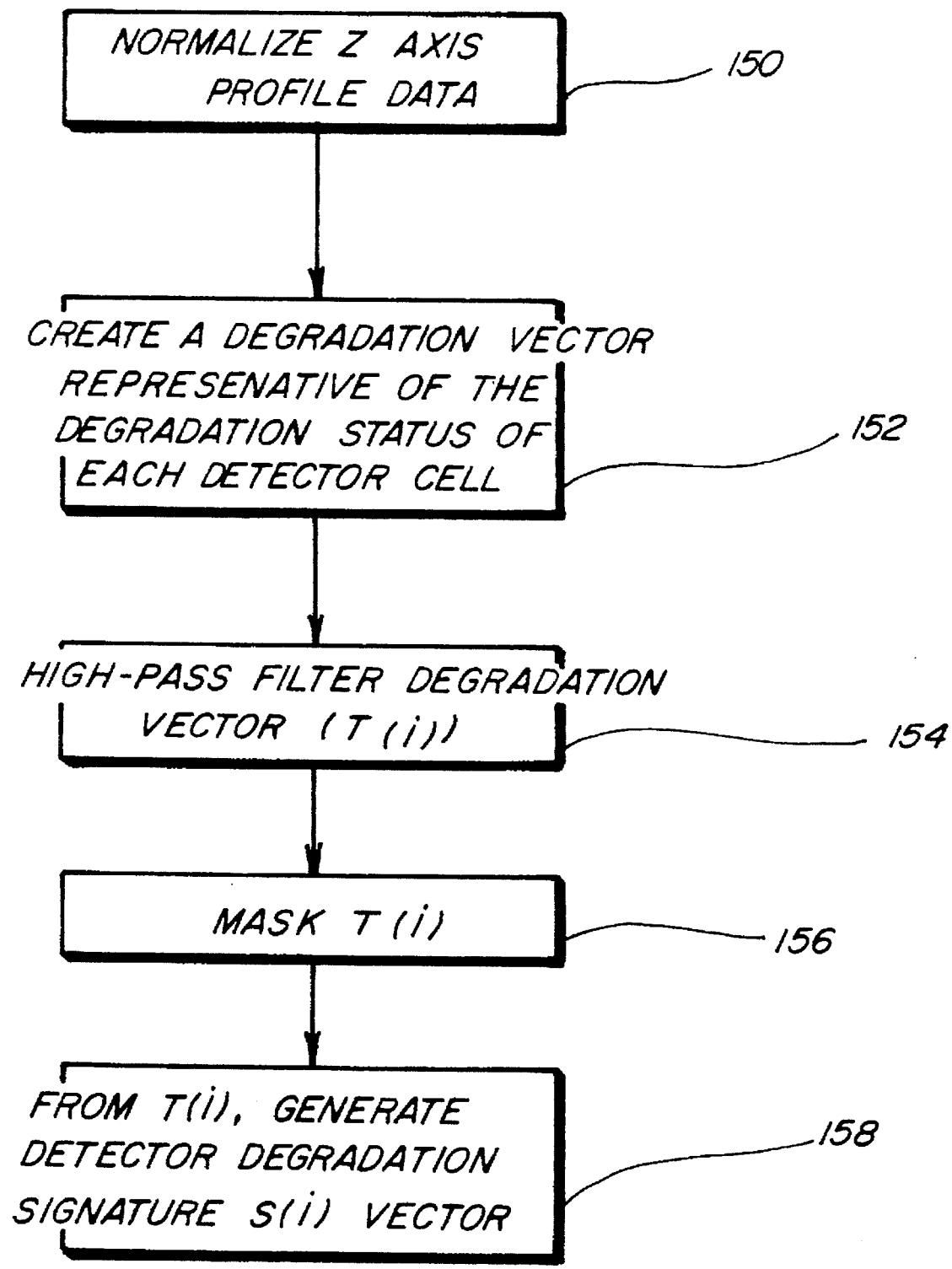
FIG. 4 is a flow chart illustrating the process steps utilized to create the detector degradation signature (S(i)) vector.

In accordance with one form of the present invention, and prior to scanning a patient, a detector degradation signature (S(i)) vector is created. FIG. 4 illustrates the process steps utilized to create the detector degradation signature (S(i)) vector. Particularly, to identify the defective channels in a detector, the z-axis profile data is normalized. The z-axis profile data may be acquired, for example, by masking the detector with a very narrow slit and moving the slit at a fine increment while exposing the detector to x-ray flux. In this manner, only a small area of the detector cell is exposed to the x-ray flux at a time. The readings taken at different locations along z-axis produce a sensitive map of the detector. A map of the detector, of course, may be generated using other techniques. For example, a narrow x-ray beam may be swept across the detector using a pre-patient collimator.

To ensure the accuracy of the detector deterioration assessment, only the portion of the data that corresponds to the actual scan exposure is used. For example, if the image to be corrected is 10 mm in slice thickness, only the center 20 mm profile on the detector is used. For example, for a 10 mm slice, the exposed area on a detector is roughly 17.5 mm. Considering the drift of the x-ray focal spot due to thermal and mechanical movement, a margin is added on each side of the cell to cover the entire area that could be exposed to the x-ray flux during the scan. For the same reason, the z-axis profile that is used for a 5 mm scan is roughly the center 11 mm.

The normalized profile is obtained by dividing the active portion of the profile by its average. The average value is used as a normalization factor since it is more reliable than the maximum value. For an ideal detector, this should result in a profile with a constant magnitude of "1".

Next, a degradation vector representative of the degradation status of each detector channel i, D(i), is created 152. Such vector may be created using the following formula:

$$D(i) = \int_{-a}^{a} |(1 - N(z,i))|/(N(z,i)) dz \qquad (1)$$

where N(z,i) is the normalized z-axis profile for channel i, and $[-\alpha, \alpha]$ denote the active region of the z-axis profile. The term inside the integration symbol is the absolute percent error of the detector profile. Vector D(i) represents the area under the absolute percent error curve over the entire active area. In general, a higher value in vector D(i) indicates a more degraded detector channel.

If every detector cell is degraded in the same manner, no ring or band artifact will occur. Therefore, it is preferred to estimate the detector degradation based on the "channel to channel" errors rather than the absolute error. To accomplish this objective, the degradation vector D(i) is high-pass filtered 154 to obtain the true channel to channel variation, T(i):

$$T(i) = |D(i) - med[D(i)]| \qquad (2)$$

where med is a nine point median filter. A median filter is used to preserve the isolated multi-channel spikes in the degradation vector.

Based on studies, it has been determined that almost all the degraded detector cells are isolated to the boundary channels. Therefore, to eliminate the unnecessary search process, the resulting vector in Equation (2) is masked 156 to preserve only the 4 boundaries cells for each module (2 cells at each end of a module). Since every detector cell is expected to experience some type of degradation during its life, it is very important to identify only those cells that have developed safety related degradation. This can be accomplished by a simple thresholding operation on the detector degradation vector T(i) to arrive at the final detector degradation signature S(i) 158:

$$S(i) = \begin{cases} T(i) & \text{if } T(i) \geq t \\ 0 & \text{if } T(i) < t \end{cases} \quad (3)$$

Any error whose magnitude is less than the threshold will be set to zero. In vector S(i) the non-zero elements correspond to the degraded cells. This vector is provided as an input to the ringfix algorithm to provide "guidance" to the correction as explained below.

With respect to performing ring artifact correction, and after an image is generated from a set of projection data, the image data is scanned to identify rings and bands. Algorithms for performing such detection are generally well known, such as the algorithm described in U.S. Pat. No. 4,670,840. The filter kernel size for performing detection is determined based on the vector S(i). Particularly, if there are two or more adjacent degraded channels, e.g., as established from vector S(i),, the rings will be wider. Therefore, the filter should be adjusted to detect wider rings. When the DFOV is reduced, the filter kernel length increases only slightly to improve the ring detection. For a standard convolution filter, a 9-point boxcar filter is used in the ringfix correction for DFOV up to 24 cm, and a 7-point for other DFOV.

Figure 5:
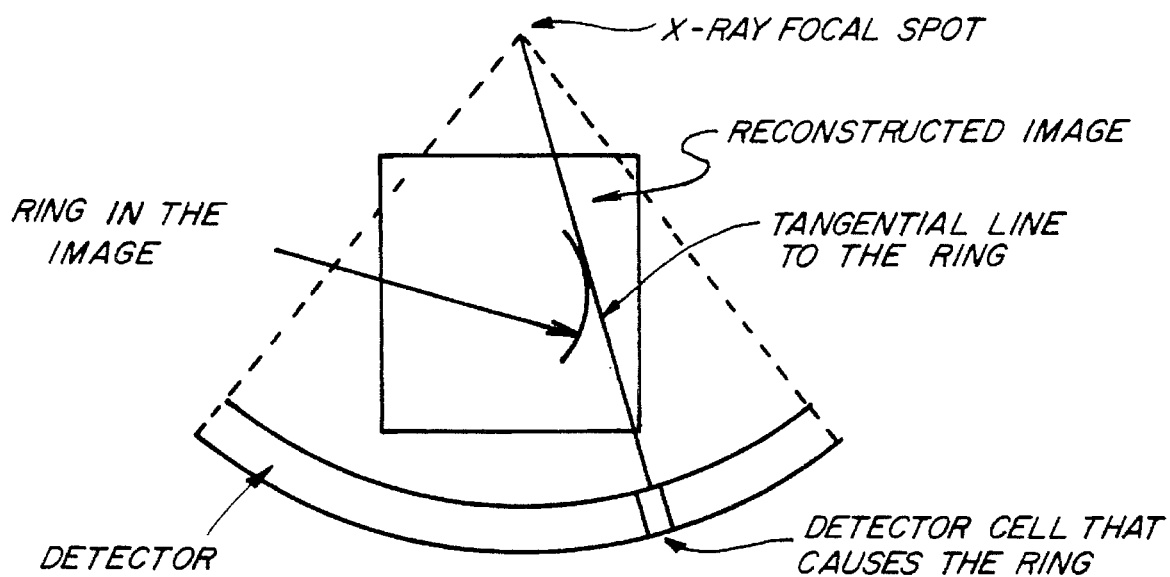
FIG. 5 illustrates mapping a detected ring to a particular detector cell.
Figure 6:
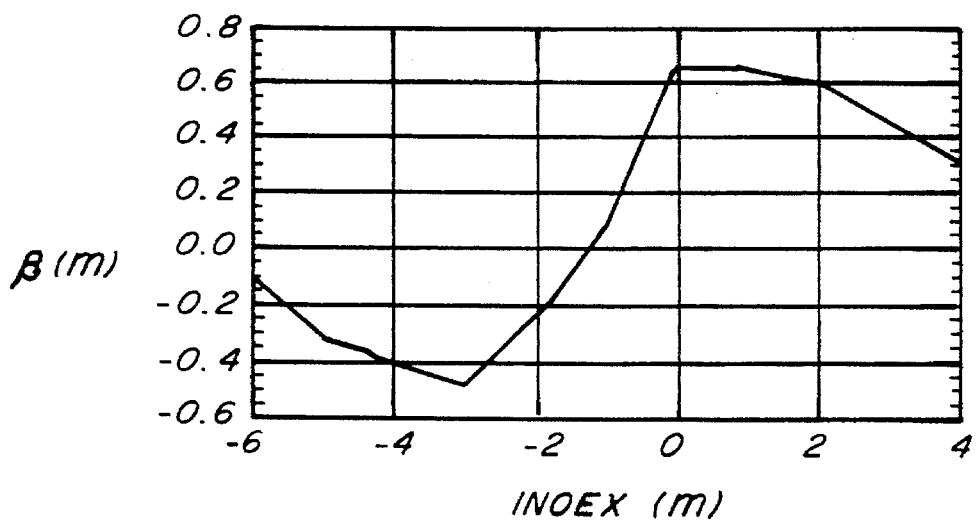
FIG. 6 illustrates a weighting factor.

Once a ring is identified, the ring is mapped to the detector cell(s) that contributed to such ring. FIG. 5 illustrates the geometry utilized in performing such mapping. The detector cells contributing to the ring are then identified. Using the vector S(i), it is determined if the ring is associated with any of the degraded cells. If a detected ring is associated with one of the cells identified by vector S(i) as a degraded cell, then the magnitude of the ring error for channel i associated with each ring segment is examined. If the magnitude is larger than a predefined threshold, (e.g., 0.5) the errors for the neighboring rings in the segment (including channel i) are modified by applying the following function to the image data:

$$e(i+m,k) = e(i+m,k) + w(i+m)\beta(m)e(i,k) \text{ For } -L \leq m < N \quad (4)$$

where e(n,k) is the error associated with detector channel n and ring segment k, w(n) is a "bat wing" type of weighting factor to account for the characteristics of backprojection, and β(m) is a weighting factor. Note that β(m) changes with the tomographic reconstruction filter and the reconstruction DFOV. FIG. 6 shows an example of the weighting factor, β(m), for a standard filter and a DFOV of 15 cm.

Once the error data is so modified, such modified error data is subtracted from the image data. The true image is then reconstructed from the corrected image data.

As explained above, the present algorithm utilizes a priori knowledge of the detector status to guide the ringfix correction. The advantage of this approach is not only its effectiveness in removing ring artifacts related to the degraded detectors, but also its minimal impact on the computational requirements.

From the foregoing description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for removing artifacts from image data due to detector degradation, the data being obtained from a CT system including a detector and an x-ray source, the detector being formed from a plurality of detector cells, a detector degradation signature vector representative of the degradation of the detector cells being generated prior to scanning a patient, a filter algorithm being used to determine whether a ring error is present in the image data, said method comprising the steps of:

for any identified ring, identifying a detector cell which contributed to creation of such ring;

determining, from the degradation signature vector, whether the identified cell is a degraded cell; and if the identified cell is a degraded cell, performing ring error correction processing on the image data.

2. A method in accordance with claim 1 wherein generating the detector degradation signature (S(i)) vector comprises the steps of:

normalizing z-axis profile data;

generating a degradation status (D(i)) vector representative of the degradation status of each detector;

high-pass filtering the degradation status vector to obtain a vector (T(i)) containing only high frequency data;

masking vector T(i) to retain a predetermined number of boundary cells; and generating the detector degradation signature (S(i)) vector from the masked vector T(i).

3. A method in accordance with claim 2 wherein generating a degradation status (D(i)) vector representative of the degradation status of each detector is performed in accordance with the following function:

$$D(i) = \int_{-a}^{a} |(1 - N(z,i))|/(N(z,i))dz$$

where N(z.i) is the normalized z-axis profile for channel i. and [−α, α] denote the active region of the z-axis profile.

4. A method in accordance with claim 2 wherein high-pass filtering the degradation status vector to obtain a vector (T(i)) containing only high frequency data is performed in accordance with the following function:

$$T(i) = D(i) - med[D(i)]$$

where med is a nine point median filter.

5. A method in accordance with claim 2 wherein generating the detector degradation signature (S(i)) vector from the masked vector T(i) is performed in accordance with the following function:

$$S(i) = \begin{cases} T(i) & \text{if } T(i) \geq t \\ 0 & \text{if } T(i) < t. \end{cases}$$

6. A method in accordance with claim 1 wherein performing ring error correction processing on the image data comprises the steps of:

determining if the magnitude of ring error for the identified cell is larger than a predetermined threshold; and if such ring error magnitude is larger than the predetermined threshold, modifying the error data by the following function:

$$e(i+m,k)=e(i+m,k)+w(i+m)\beta(m)e(i,k) \text{ For } -L<m<N$$

where e(n,k) is the error associated with the detector channel n and ring segment k, w(n) is a bat wing type of weighting factor to account for the characteristics of backprojection, and $\beta(m)$ is a weighting factor; and subtracting the modified error data from the image data.

7. A method in accordance with claim 1 wherein identifying the detector cell which contributed to creation of the ring comprises the step of mapping the ring to at least one detector cell.

8. A method in accordance with claim 1 wherein, based on the detector degradation signature vector S(i), the filter algorithm for detecting ring error is modified.

9. A system for producing a tomographic image of an object from data acquired in a helical scan, said system comprising a detector having a plurality of detector cells, a detector degradation signature (S(i)) vector being created prior to scanning a patient and stored in a memory unit of the system, said system further comprising a computer coupled to said detector and said memory unit, said computer programmed to correct the image data obtained from said detector cells for any ring error resulting from detector cell degradation by:

subsequent to scanning the patient, if the image data contains a ring error, identifying a detector cell contributing to the ring error;

determining, from the detector degradation signature vector, if the identified cell is a degraded cell; and if the identified cell is a degraded cell, performing ring error correction processing on such data.

10. A system in accordance with claim 9 wherein said computer is programmed to generate a detector degradation signature (S(i)) vector prior to scanning a patient by:

normalizing z-axis profile data;

generating a degradation status (D(i)) vector representative of the degradation status of each detector;

high-pass filtering the degradation status vector to obtain a vector (T(i)) containing only high frequency data;

masking vector T(i) to retain a predetermined number of boundary cells; and generating the detector degradation signature (S(i)) vector from the masked vector T(i).

11. A system in accordance with claim 10 wherein generating a degradation status (D(i)) vector representative of the degradation status of each detector is performed by said computer in accordance with the following function:

$$D(i)=\int_{-a}^{a} |(1-N(z,i))|/(N(z,i))dz$$

where N(z,i) is the normalized z-axis profile for channel i, and $[-\alpha, \alpha]$ denote the active region of the z-axis profile.

12. A system in accordance with claim 10 wherein high-pass filtering the degradation status vector to obtain a vector (T(i)) containing only high frequency data is performed by said computer in accordance with the following function:

$$T(i)=D(i)-med[D(i)]$$

where med is a nine point median filter.

13. A system in accordance with claim 10 wherein generating the detector degradation signature (S(i)) vector from the masked vector T(i) is performed by said computer in accordance with the following function:

$$S(i)=\begin{cases} T(i) & \text{if } T(i) \geq t \\ 0 & \text{if } T(i) < t. \end{cases}$$

* * * * *